United States Patent [19]

Maumy et al.

[11] Patent Number: 4,486,349

[45] Date of Patent: Dec. 4, 1984

[54] PROCESS FOR PREPARING PARA-QUINONE OR ORTHO-QUINONE DERIVATIVES, POSSIBLY ALKOXYLATED OR ARYLOXYLATED, RESPECTIVELY FROM THE CORRESONDING HYDROQUINONE OR PYROCATECHIC DERIVATIVES

[75] Inventors: Michel Maumy, Bois Colombes; Patrice J. G. Capdevielle; Philippe L. Dostert, both of Paris; Michel Langlois, Buc, all of France

[73] Assignee: Delalande, S.A., France

[21] Appl. No.: 441,273

[22] Filed: Nov. 12, 1982

[30] Foreign Application Priority Data

Nov. 18, 1981 [FR] France .................................. 81 21606
Nov. 5, 1982 [FR] France .................................. 82 18607

[51] Int. Cl.³ ........................ C07C 50/04; C07C 50/06
[52] U.S. Cl. .............................. 260/239 A; 260/239 B; 260/239 EQ; 260/396 R; 544/174; 544/391; 548/539; 546/206; 546/226; 568/630
[58] Field of Search ........ 260/396 R, 239 EQ, 239 A, 260/239 B; 544/174, 391; 548/539; 546/206, 226; 568/630

[56] References Cited

U.S. PATENT DOCUMENTS

| 3,213,114 | 10/1965 | Braxton, Jr. et al. | 260/396 R |
| 3,870,731 | 3/1975 | Hutchings | 260/396 R |
| 3,987,068 | 10/1976 | Reilly | 260/396 N |
| 4,153,810 | 5/1979 | Neumann et al. | 568/630 |
| 4,208,339 | 6/1980 | Costantini et al. | 260/396 R |
| 4,235,790 | 11/1980 | Müller et al. | 260/396 R |
| 4,257,968 | 3/1981 | Reilly | 260/396 R |

*Primary Examiner*—Richard L. Raymond
*Assistant Examiner*—Raymond Covington
*Attorney, Agent, or Firm*—Schiller & Pandiscio

[57] ABSTRACT

Process for preparing a para-quinone or ortho-quinone derivative, possibly alkoxylated or aryloxylated, which consists in oxidizing respectively the corresponding hydroquinone or pyrocatechic derivative, by means of the complex prepared, in situ or separately, by combining a cuprous salt, a hydrocarbon substituted by a cyano group and molecular oxygen, the oxidation being possibly carried out in the presence of an alkoxylating or aryloxylating agent of the hydroxylated derivative type.

13 Claims, No Drawings

PROCESS FOR PREPARING PARA-QUINONE OR ORTHO-QUINONE DERIVATIVES, POSSIBLY ALKOXYLATED OR ARYLOXYLATED, RESPECTIVELY FROM THE CORRESONDING HYDROQUINONE OR PYROCATECHIC DERIVATIVES

The present invention relates to a new process for preparing a para-quinone or ortho-quinone derivative, possibly alkoxylated or aryloxylated.

Such derivatives form undeniably important compounds for the chemical and parachemical industries, where they are more especially used for the synthesis of certain dyes, insecticides and pharmaceutical products.

However, the processes and techniques used up to the present time for preparing such derivatives are often complex, expensive, difficult to put into practice industrially and only lead to the desired derivatives with unsatisfactory yields.

The applicant has for this reason been led to study new methods of synthesis and he has thus perfected, and this is the first object of the present invention, a new process for preparing a para-quinone or ortho-quinone derivative respectively from the corresponding hydroquinone or pyrocatechic derivative, which is characterized in that it consists in oxidizing said hydroquinone or pyrocatechic derivative by means of the complex prepared, in situ or separately, by combining a cuprous salt, a hydrocarbon substituted by a cyano group and molecular oxygen.

It appears in fact that when these three elements are placed in presence, a cupric complex is formed which is responsible for the desired oxidization. As cuprous salt, any salt may be used which is capable of existing equally in a cupric form and forming a complex with the hydrocarbon substituted by a cyano group, this latter being more particularly chosen from the cyanoalkanes. However, it is more especially preferable to use the cuprous chloride—acetonitrile couple, the cuprous chloride like the corresponding cupric chloride having excellent solubility in acetonitrile.

The particular combination of cuprous chloride, acetonitrile and molecular oxygen, already described in U.S. Pat. No. 3,987,068 leads to the formation of an isolable complex which is in the form of a product dark brown in color, has the empirical formula $Cu_4Cl_4O_2(CH_3CN)_3$ determined by the following conventional analytical methods:

titration of the copper ($Cu^{II}$) by iodometry: calculated %: 46.12 obtained %: 46.44 titration of chlorine (gravimetry of AgCl): calculated %: 25.73 obtained %: 25.64 acidimetric titration (pHmeter): obtained: 4.05 basic equivalents for $4Cu^{II}$, that is two oxo($O^{2-}$) functions for 4 copper atoms,
and contains the pattern $Cl-Cu^{II}O^2-Cu^{II}-Cl$ or $Cl-Cu^{II}-O-Cu^{II}-Cl$.

It should further be noted that this complex is able to fix water so as to give a hydrated complex, green in color, which has qualitatively the same properties as the anhydrous complex, but acts nevertheless more slowly on the different substrates to be oxidized.

It will further be noted that the molecular oxygen may be used in the form of pure oxygen, atmospheric oxygen or oxygen mixed with one or several gases which are inert with respect to the complex and with respect to the substrate to be oxidized.

The amount of hydrocarbon substituted by a cyano group used should be sufficient to dissolve the cuprous salt and to share in the formation of the complex.

The process of the invention will be carried out in a solvent or a mixture of solvents in which the complex formed and the substrate to be oxidized are soluble. Thus, in the case where the cuprous salt is cuprous chloride and the hydrocarbon with cyano substitution is acetonitrile, the process of the invention will be advantageously carried out in acetonitrile, a particularly good solvent for the cuprous complex $Cu_4Cl_4O_2(CH_3CN)_3$ or, if acetonitrile is not a good solvent of the substrate to be oxidized, in a mixture of acetonitrile and one or more aprotic organic solvents capable of dissolving said substrate and inert with respect to the cuprous complex, such as methylene chloride.

When the separately prepared complex is used, it is advantageous to carry out the oxidization in a molecular oxygen atmosphere, preferably under a molecular oxygen partial pressure of the order of one atmosphere. Similarly, when the process of the invention is used by preparing the complex in situ, the molecular oxygen is used so that its partial pressure is of the order of the atmospheric pressure.

It should be noted that a molecular oxygen pressure which is unduly higher than the normal pressure may cause a profound modification of the reaction mechanism and, thus, prevent the desired quinones from being obtained satisfactorily.

The amount of cuprous salt or of cupric complex to be used is equal respectively to at least four or at least one equivalent with respect to the substrate to be oxidized. However, when the oxidization reaction is effected in an oxygen atmosphere, it is sufficient to use the cuprous salt and the cupric complex in catalytic amounts for it seems in fact that the molecular oxygen permanently regenerates the cupric complex consumed during the reaction.

The hydroquinone or pyrocatechic nucleus of the derivative to be oxidized may be substituted or not; in the case of the pyrocatechic nucleus it is nevertheless preferable for the possible substituent(s) to be different from the hydroxyl radical for in some cases the presence of this type of radical may prevent the formation of the desired quinone derivative.

At the end of the reaction, the quinone derivative formed will be advantageously isolated by eliminating the solvent(s) and by extracting with different organic solvents in which the cuprous salt and the cupric complex are insoluble; such solvents are formed for example by ether, ethyl acetate, methylene chloride and mixtures thereof.

It will of course be preferable to use the anhydrous cupric complex rather than the corresponding hydrate, since, as was mentioned above, this latter acts only slowly on the substrates to be oxidized.

It is certain that if the aromatic derivative to be oxidized comprises a substituent capable of reacting with the cupric complex, and this will for example be the case for an acid group (particularly a carboxyl group) capable of forming a copper salt, this group may be blocked, if so desired and to the extent possible, for example by forming the ester in the case of the carboxyl group and hydrolizing the ester group once the reaction has finished. Failing such blocking, it will be advisable to operate in the presence of larger amounts of the cupric complex, than those normally required.

The oxidization reaction in accordance with the invention leads to the desired quinone derivatives with particularly interesting yields and this, even when operating at ambient temperature.

It will finally be noted that this oxidization reaction will be advantageously carried out in the presence of a desiccant agent, such as sodium, calcium or magnesium sulfate, which is intended to fix the water formed during the reaction, which water may in some cases seriously hinder the reaction process and/or impair the desired quinone derivative if this latter is sensitive to water.

The applicant has further demonstrated that if the oxidization reaction of a hydroquinone or pyrocatechic derivative is carried out as outlined above but in the presence of an alkoxylating or aryloxylating agent of the hydroxylated derivative type, it is possible to carry out simultaneously with said oxidization, an alkoxylation or aryloxylation reaction for introducing the alkoxy or aryloxy group of the alkoxylating or aryloxylating agent used into the molecule to be oxidized. With this embodiment consequently, the para-quinone or ortho-quinone derivative, whose para-quinone or ortho-quinone nucleus is alkoxylated or aryloxylated, may be respectively obtained from a hydroquinone or pyrocatechic derivative.

It seems in fact that the combination of the cuprous salt, the hydrocarbon with cyano substitution, the molecular oxygen and the alkoxylating or aryloxylating agent leads to the formation of a complex responsible for the simultaneous oxidization and alkoxylation or aryloxylation reaction; the same complex is obtained by mixing said alkoxylating or aryloxylating agent and the cupric complex which is previously prepared by combining the cuprous salt, the hydrocarbon and the molecular oxygen.

It has been discovered that the simultaneous oxidization and alkoxylation or aryloxylation of the hydroquinone derivative could be obtained with particularly interesting results when the hydroquinone nucleus carried at least one electroattracting substituent. Thus, the starting hydroquinone derivative may correspond more especially to the formula:

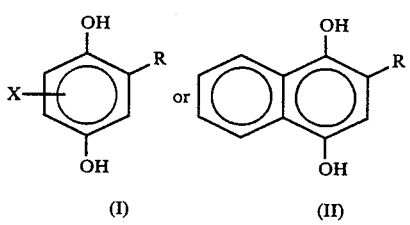

where:
R represents an electroattracting group, and
X designates a hydrogen or a halogen atom; a $R_1$ or $OR_1$ group, $R_1$ designating an alkyl group with 1 to 5 carbon atoms, a cycloalkyl group with 3 to 7 carbon atoms, a cycloalkylalkyl group with 4 to 10 carbon atoms, or a benzyl group substituted or not by one or more halogen atoms or by one or more methyl or methoxy groups; or a phenoxy group substituted or not by one or more halogen atoms or by one or more methyl or methoxy groups, and the alkoxylating or aryloxylating agent may correspond to the formula;

$R_2$—OH (III)

in which $R_2$ designates:
an $R_1$ group having the same meaning as above,
an allyl or methallyl chain,
a $(Y)_n C(H)_{3-n}$—$(CH_2)_m$— chain where Y represents a halogen atom, n=1, 2 or 3 and m=1, 2 or 3,
a phenyl nucleus having the structure

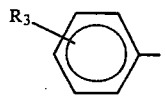

where $R_3$=$NO_2$, CN, CHO, $COR_1$ or $COOR_1$, $R_1$ having the same meaning as previously, or
a benzyl group or a group of structure

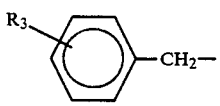

where $R_3$ has the same meaning as above,
the alkoxylated or aryloxylated para-quinone derivative obtained corresponding then to the formula:

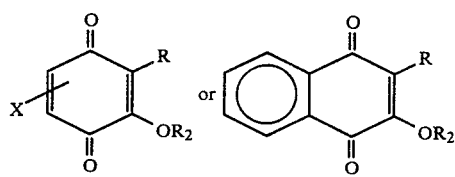

where X, R and $R_2$ have the same meanings as before.

As for the electroattracting group, the following groups may be more particularly mentioned: formyl; $COR_1$ or $COOR_1$ where $R_1$ has the same meaning as before; aminocarbonyl; $CONHR_1$ or $CONR_4R_5$ where $R_4$ and $R_5$ have the same meaning as $R_1$, $R_1$ having the same meaning as before or $R_4$ and $R_5$ form jointly with the nitrogen atom to which they are linked, a heterocyclic radical chosen from the following: aziridino, azetidino, pyrrolidino, piperidino, hexamethyleneimino, morpholino or (4-methyl) piperizino; cyano.

Moreover, the pyrocatechic derivative may more particularly correspond to the formula:

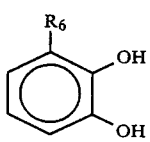

where $R_6$ represents a hydrogen or halogen atom or a $R_1$, $OR_1$, $COR_1$ or $COOR_1$ group, $R_1$ having the same meaning as before and the alkoxylating or aryloxylating agent may correspond to the above-defined formula $R_2$—OH(III), the alkoxylated or aryloxylated ortho-quinone derivative then being formed by the compound of formula:

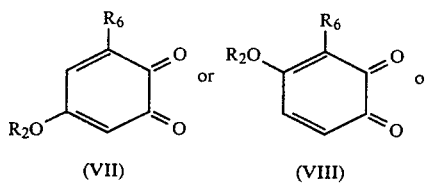

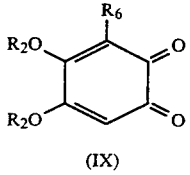

or by the mixture of at least two of these compounds, depending on the nature of $R_6$ and on the amount of agent $R_2$—OH used, $R_2$ and $R_6$ having the same meaning as before.

Some $R_6$ substituents in fact allow the reaction to be preferentially orientated towards the compound of formula (VII) or towards the compound of formula (VIII); thus, for example when $R_6$ represents the methoxy group, the reaction leads exclusively to the compound of formula (VII). Furthermore, depending on the amount of alkoxylating or aryloxylating agent used, the reaction does not stop at the stage of the compound of formula (VII) or of formula (VIII) or at the mixture of these compounds, but continues as far as the formation of the dialkoxylated or diaryloxylated compound of formula (IX).

The starting pyrocatechic derivative may also correspond to the formula:

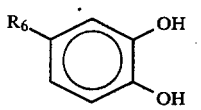

where $R_6$ has the same meaning as in formula (VIa) and when the alkoxylating or aryloxylating agent corresponds to the above-defined formula $R_2$—OH (III), the alkoxylated or aryloxylated ortho-quinone derivative obtained corresponds to the formula:

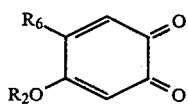

where $R_6$ and $R_2$ have the same meaning as in formula (VIb) and in formula (III) respectively.

According to a first embodiment of the simultaneous oxidization and alkoxylation or aryloxylation process, the oxidizing cupric complex is first of all prepared separately or in situ, by combining a cuprous salt and a hydrocarbon substituted by a cyano group, this combination being realized in the presence of molecular oxygen (pure oxygen, atmospheric oxygen or any other gaseous mixture of oxygen and of a gas or gases inert with respect to the complex and with respect to the substrate to be oxidized and alkoxylated or aryloxylated). Contacting of the oxygen with the salt and with the hydrocarbon may be carried out by simple bubbling and/or with agitation in an oxygen atmosphere (or in an oxygen-containing gas atmosphere). The oxidizing cupric complex thus formed is placed in contact, with agitation, with the alkoxylating or aryloxylating agent, in an appropriate solvent formed by the hydrocarbon having served for preparing the complex or by the mixture of said hydrocarbon and an aprotic solvent (for example, methylene chloride or ethyl acetate) if the substrate is not very soluble in said hydrocarbon, and preferably in the presence of a desiccating agent. The resulting mixture is then brought into contact with the substrate to be treated; in the case where the substrate is formed by a pyrocatechic derivative, the best yields in ortho-quinone derivative are generally obtained by gradually introducing in said mixture, preferably over three or four hours, said pyrocatechic derivative in solution in the previously defined hydrocarbon with cyano substitution possibly admixed with the aprotic solvent also defined above.

The contacting of said mixture with the substrate is advantageously carried out with agitation in a molecular oxygen atmosphere (pure oxygen or a mixture of oxygen and an inert gas or gases) and under a substantially normal oxygen partial pressure.

According to a second embodiment of the simultaneous oxidization and alkoxylation or aryloxylation process, the complex responsible for the simultaneous oxidization and alkoxylation or aryloxylation reaction is formed within the mixture formed by the substrate to be treated, the alkoxylating or aryloxylating agent and a possible desiccant, in solution in the cyano substitution hydrocarbon possibly admixed with the above-defined aprotic solvent if the substrate is not very soluble in said hydrocarbon. The formation of said oxidoalkoxylation or oxidoaryloxylation complex is achieved more especially by introducing cuprous chloride into the mixture which has just been defined, with agitation and in the presence of molecular oxygen. It is more particularly preferable to operate in a molecular oxygen atmosphere (pure oxygen or a mixture of oxygen and an inert gas or gases) under a substantially normal oxygen partial pressure.

The desiccating agent, which as before may for example be sodium, calcium, or magnesium sulfate, is intended to fix the water produced during oxidization and alkoxylation and aryloxylation, the amount of desiccant agent used being preferably chosen so as to ensure the fixing of at least two water equivalents.

Since the complex responsible for the oxidization and the alkoxylation or aryloxylation, consumed during the reaction, is permanently regenerated by the molecular oxygen, it is in principle sufficient to use cuprous salt in a catalytic amount but it is nevertheless preferable to use it at the rate of two equivalents, the amount of alkoxylating or aryloxylating agent used being usually chosen in the range from 1 to 10 equivalents.

Finally, the simultaneous oxidization and alkoxylation or aryloxylation process presents the advantage of being able to be carried out at ambient temperature and, generally, the reaction temperature may be between zero and 50° C. for a reaction time of 3 to 4 hours.

The following preparations are given by way of examples to illustrate the invention.

EXAMPLE 1

Preparation of the cupric complex and its hydrate 1 g of cuprous chloride in 20 ml of acetonitrile absorbs 60 ml of pure oxygen in 10 hours at 23° C. (0.25 equivalent/$Cu^I$); the major part of the cupric complex formed is then precipitated in the form of a dark brown powder which is drained on sintered glass (porosity no. 3), maintained for an hour in a stream of dry air and dried for 2 days under vacuum in a desiccator. 1.26 g of dry complex are isolated (yield: 90%).

The hydrate may be obtained by adding water to the anhydrous complex previously obtained or else by repeating the above-described operating method for preparing the anhydrous complex but operating in the presence of water.

EXAMPLE 2

Preparation of 3,5 di-tertiobutyl orthobenzoquinone

A mixture of 4 g of 3,5-di-tertiobutyl pyrocatechol and 5 g of cuprous chloride in 50 ml of acetonitrile is agitated in an oxygen atmosphere (normal pressure) for two hours. Then the solvent is evaporated, the residue extracted with ethyl ether, the extraction solvent is concentrated to 8 ml, the residue is diluted in 40 ml of pentane, the solution is cooled to $-20°$ C. and the precipitate of 3,5-di-tertiobutyl orthobenzoquinone obtained is filtered (melting point=114° C.)—Weight: 3.4 g.

By the process of example 2, are also obtained, by way of non limiting examples:

2-methyloxycarbonyl benzoquinone, from the methyl ester of 2,5-dihydroxybenzoic acid, 2-acetyl benzoquinone, from 2,5-dihydroxyacetophenone.

EXAMPLE 3

2-Acetyl 3-benzyloxypara-benzoquinone (IV)

To a solution of 4 g of 2-acetyl hydroquinone (I) in 90 ml of ethyl acetate, 100 ml of acetonitrile and 5 ml of benzyl alcohol (III) are added 60 g of crushed calcium sulfate oven dried at 240° C., then 8.5 g of powdered cuprous chloride. It is agitated in gaseous oxygen (at a pressure of one atmosphere) for two hours and thirty minutes at ambient temperature. Then it is diluted with toluene, filtered, the filtrate is evaporated, the residue taken up in a mixture of 120 ml of ether and 80 ml of cyclohexane; by trituration of the resulting mixture followed by a filtration separation of the insoluble matter, a solution is obtained which leads to the expected compound (Yield≃70%) after evaporation of the solvents.

EXAMPLE 4

4-Methyl 5-(para nitrophenoxy) orthobenzoquinone (X)

10 g of cuprous chloride in 100 ml of acetonitrile are agitated for 3 hours 30 min. in gaseous oxygen (at a pressure of one atmosphere). A black precipitate is formed. Then 7 g of para-nitrophenol(III) and 15 g of anhydrous sodium sulfate are added and agitation is carried out for a further hour; a solution of 5.2 g of 4-methyl pyrocatechol (VIb) in 30 ml of acetonitrile is then gradually added to the mixture in three hours thirty minutes under an oxygen pressure of one atmosphere and with good agitation. After a further hour and fifteen minutes, the solvent is evaporated under vacuum and the residue is taken up with 150 ml of ethyl acetate. After conventional extraction and purification, the expected product is obtained (Yield≃60%).

By one or other of the processes of the preceding examples 3 or 4, there are also obtained, by way of non limiting examples:

2-acetyl 3-methoxy para-benzoquinone, from 2-acetyl 1,4-dihydroxybenzene, 2-acetyl 3-(2-chloro ethoxy-1) para-benzoquinone, from 2-acetyl 1,4-dihydroxybenzene, 2-formyl 3-methoxy para benzoquinone, from 2-formyl 1,4-dihydroxybenzene, 2-formyl 3-benzyloxy para-benzoquinone, from 2-formyl 1,4-dihydroxybenzene, 2-formyl 3-methoxy 5-methylpara-benzoquinone, from 2-formyl 5-methyl 1,4-dihydroxybenzene, 2-acetyl 3-benzyloxy (and 3-[2-chloro ethoxy-1]) 1,4-naphtoquinones, from 2-acetyl 1,4-dihydroxynaphtalene, 3-methoxy 5-(para-nitrobenzyloxy) ortho-benzoquinone, from 3-methoxy 1,2-dihydroxybenzene.

We claim:

1. A process for preparing a para-quinone or ortho-quinone derivative respectively from the corresponding hydroquinone or pyrocatechic derivative, characterized in that it consists in oxidizing said hydroquinone or pyrocatechic derivative by means of the complex prepared, in situ or separately, by combining a cuprous salt, a hydrocarbon substituted by a cyano group and molecular oxygen.

2. The process according to claim 1, characterized in that the cuprous salt and the hydrocarbon substituted by a cyano group are respectively cuprous chloride and acetonitrile.

3. The process according to claim 1 or 2, using the separately prepared complex, characterized in that oxidization is carried out in a molecular oxygen atmosphere.

4. The process according to claim 1 or 2, characterized in that oxidization is carried out under a molecular oxygen partial pressure of the order of one atmosphere.

5. The process according to claims 1 or 2 characterized in that oxidization is carried out in the presence of a desiccant agent.

6. A process for preparing a para-quinone or ortho-quinone derivative whose para-quinone or ortho-quinone nucleus is alkoxylated or aryloxylated, characterized in that it consists in oxidizing respectively the corresponding hydroquinone or pyrocatechic derivative in accordance with the process as claimed in claims 1 or 2 and in the presence of an alkoxylating or aryloxylating agent of the hydroxylated derivative type.

7. The process according to claim 6, characterized in that the hydroquinone nucleus of the hydroquinone derivative carries at least one electro-attracting substituent.

8. The process according to claim 6, characterized in that the starting hydroquinone derivative corresponds to the formula:

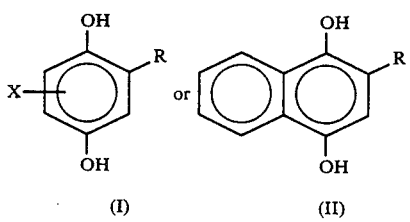

where:

R represents an electro-attracting group, and

X designates a hydrogen or halogen atom; an $R_1$ or $OR_1$ group, $R_1$ designating an alkyl group with 1 to 5 carbon atoms, a cycloalkyl group with 3 to 7 carbon atoms, a cycloalkylalkyl group with 4 to 10 carbon atoms or a benzyl group substituted or not by one or more halogen atoms or by one or more methyl or methoxy groups; or a phenoxy group substituted or not by one or more halogen atoms or by one or more methyl or methoxy groups;
and in that the alkoxylating or aryloxylating agent corresponds to the formula:

$$R_2\text{—OH} \qquad (III)$$

in which $R_2$ designates:
- an $R_1$ group having the same meaning as above,
- an allyl or methallyl chain,
- a $(Y)_n C(H)_{3-n}$—$(CH_2)_m$— chain where Y represents a halogen atom, $n = 1$, 2 or 3 and $m = 1$, 2 or 3,
- a phenyl nucleus of structure

[structure: $R_3$-phenyl-]

where $R_3 = NO_2$, CN, CHO, $COR_1$ or $COOR_1$, $R_1$ having the same meaning as before, or a benzyl group or a group of structure

[structure: $R_3$-phenyl-$CH_2$—]

where $R_3$ has the same meaning as above, the alkoxylated or aryloxylated para-quinone derivative obtained corresponding to the formula:

(IV) / (V)

where X, R and $R_2$ have the same meanings as before.

9. The process according to claim 8, characterized in that the electro-attracting group is chosen from the following groups: formyl; $COR_1$ or $COOR_1$ where $R_1$ has the same meaning as in claim 8; aminocarbonyl; $CONHR_1$ or $CONR_4R_5$ where $R_4$ and $R_5$ have the same meaning as $R_1$, $R_1$ having the same meaning as in claim 8 or $R_4$ and $R_5$ form jointly with the nitrogen atom to which they are linked a heterocyclic radical chosen from the following: aziridino, azetidino, pyrrolidino, piperidino, hexamethyleneimino, morpholino or (4-methyl) piperazino; cyano.

10. The process according to claim 6, characterized in that the starting pyrocatechic derivative corresponds to the formula:

(VIa)

where $R_6$ represents a hydrogen or halogen atom or a $R_1$, $OR_1$, $COR_1$ or $COOR_1$ group, $R_1$ having the same meaning as in claim 8; in that the alkoxylating or aryloxylating agent corresponds to the formula $R_2$—OH (III) defined in claim 8; and in that the alkoxylated or aryloxylated ortho-quinone derivative obtained is formed by the compound of formula:

(VII) or (VIII) or (IX)

or by the mixture of at least two of these compounds, depending on the nature of $R_6$ and on the amount of agent $R_2$—OH used, $R_2$ and $R_6$ having the same meaning as before.

11. The process according to claim 6, characterized in that the starting pyrocatechic derivative corresponds to the formula:

(VIb)

where $R_6$ has the same meaning as in claim 10 and in that the alkoxylating or aryloxylating agent corresponds to the formula $R_2$—OH(III) defined in claim 8, the alkoxylated or aryloxylated ortho-quinone derivative obtained corresponding to the formula:

(X)

where $R_6$ and $R_2$ have respectively the same meaning as in formula (VIb) and formula (III).

12. A process for preparing a para-quinone or ortho-quinone derivative whose para-quinone or ortho-quinone nucleus is alkoxylated or aryloxylated, characterized in that it consists in oxidizing respectively the corresponding hydroquinone or pyrocatechic derivate in accordance with the process as claimed in claim 4 and in the presence of an alkoxylating or aryloxylating agent of the hydroxylated derivative type.

13. A process for preparing a para-quinone or ortho-quinone derivative whose para-quinone or ortho-quinone nucleus is alkoxylated or aryloxylated, characterized in that it consists in oxidizing respectively the corresponding hydroquinone or pyrocatechic derivate in accordance with the process as claimed in claim 5 and in the presence of an alkoxylating or aryloxylating agent of the hydroxylated derivative type.

* * * * *